United States Patent [19]
Rock

[11] Patent Number: 5,102,416
[45] Date of Patent: Apr. 7, 1992

[54] VESSEL VECTOR INVASIVE CATHETER

[76] Inventor: John M. Rock, 9904 Logan Dr., Potomac, Md. 20854

[21] Appl. No.: 439,332

[22] Filed: Nov. 21, 1989

[51] Int. Cl.$^5$ .............................................. A61M 5/00
[52] U.S. Cl. ...................................... 606/194; 604/95; 604/96; 604/101
[58] Field of Search .................... 604/95, 96, 101; 128/772; 606/7, 13–17, 194

[56] References Cited

U.S. PATENT DOCUMENTS

| | | | |
|---|---|---|---|
| 3,665,928 | 5/1972 | Del Guercio | 604/95 |
| 3,811,448 | 5/1974 | Morton | 604/102 |
| 4,040,413 | 8/1977 | Ohshiro | 604/101 |
| 4,141,364 | 2/1979 | Schultze | 604/96 |
| 4,148,307 | 4/1979 | Utsugi | 604/95 |
| 4,183,102 | 1/1980 | Guiset | 604/101 |
| 4,207,872 | 6/1980 | Meiri et al. | 604/95 |
| 4,233,983 | 11/1980 | Rocco | 604/102 |
| 4,406,656 | 9/1983 | Hattler et al. | 604/96 |
| 4,685,473 | 8/1987 | Karcher et al. | 604/95 |
| 4,747,405 | 5/1988 | Leckrone | 606/7 |
| 4,758,221 | 7/1988 | Jureidini | 604/95 |
| 4,787,388 | 11/1988 | Hofmann | 606/194 |
| 4,838,859 | 6/1989 | Strassmann | 604/95 |
| 4,875,897 | 10/1989 | Lee | 604/283 |
| 4,878,495 | 11/1989 | Grayzel | 604/101 |
| 4,906,303 | 3/1990 | Maloney et al. | 604/95 |
| 4,909,787 | 3/1990 | Danforth | 604/95 |
| 4,983,165 | 1/1991 | Loiterman | 604/101 |

Primary Examiner—Max Hindenburg
Assistant Examiner—Ralph A. Lewis

[57] ABSTRACT

A catheter formed and sized to be traversed through a complex path into a desired location in the body of a human medical patient is disclosed herein. The disclosed device includes a unique means for the deflection of the distal end of the catheter such that it may be easily directed within the patient's venal system. This deflection system exploits hydrodynamic forces produced by bloodflow over distal-end surfaces which are asymmetrically distended in a controlled manner.

11 Claims, 4 Drawing Sheets

VESSEL VECTOR INVASIVE CATHETER

BACKGROUND OF THE INVENTION

1. Field of the Invention

This invention relates to the treatment of a medical patient such that the catheter possesses the capability for its distal end to be directed in a controlled manner facilitating its traversal along a tortuous path to a desired location within the patient's venal system.

2. Descrption of the Prior Art

Catheters in common invasive cardiovascular use are not maneuverable. As such there is often difficulty in directing the distal end of the catheter into the desired one of several vessels present at a circulatory bifurcation (i.e. choosing the proper vessel at a circulatory "fork in the road"). Therefore, frequent fluoroscopic pictures are needed at each bifurcation encountered while traversing the catheter to the area of procedural interest. Such a large number of images is required because of the sort of ambiguous "hit or miss" vessel selection that takes place at each bifurcation. This ambiguity is inherent in the use of present catheters which cannot be actively guided. Each such image results in further radiation exposure to patient and care providers. Necessarily then, there exists a dilemma presented to the physician in trading off exposure against the absolute need to assure proper catheter location. The maneuvering facility of this invention allows active, positive selection of the desired vessel at a bifurcation thus minimizing flu roscopic imaging (with a reduction in attendant radiation). Patient safety is furher enhanced since repeated chance probing is eliminated by positive vessel selection; this also lessens possibility of vessel wall puncture while shortening overall procedure duration and time under anesthesia.

SUMMARY

The invention is a maneuverable multifunctional intravenous catheter, inflatable at its distal extremity. It can be inflated in a symmetrical manner as in angioplasty catheters but also can be inflated *asymmetrically*. As such it can be "steered" within the tortuous path of the circulatory system. Steering is effected through displacement forces obtained by the hydrodynamic interaction of bloodflow with surfaces at the catheter's distal extremity which are deformed in controlled, asymmetrical way to constitute a hydrofoil shape. As a secondary effect that controlled asymmetrical deformation of the catheter's head-end causes off-axis deformation of the catheter's axial open core. Accordingly, devices introduced along the catheter's open axial core are deflected off-axis as well. Also as a secondary effect, the device will perform balloon angioplasty via symmetrical distension of the distal extremity. The catheter's open core also permits external monitoring of vessel pressure at the distal-end site, and/or can deliver gas or liquid to that distal-end site. The device is formed, sterilized, packaged and sealed in a sterile environment, remains so until opened for use, and it is disposable to avoid re-sterilization concerns.

PREFERRED EMBODIMENT

Figure 1:
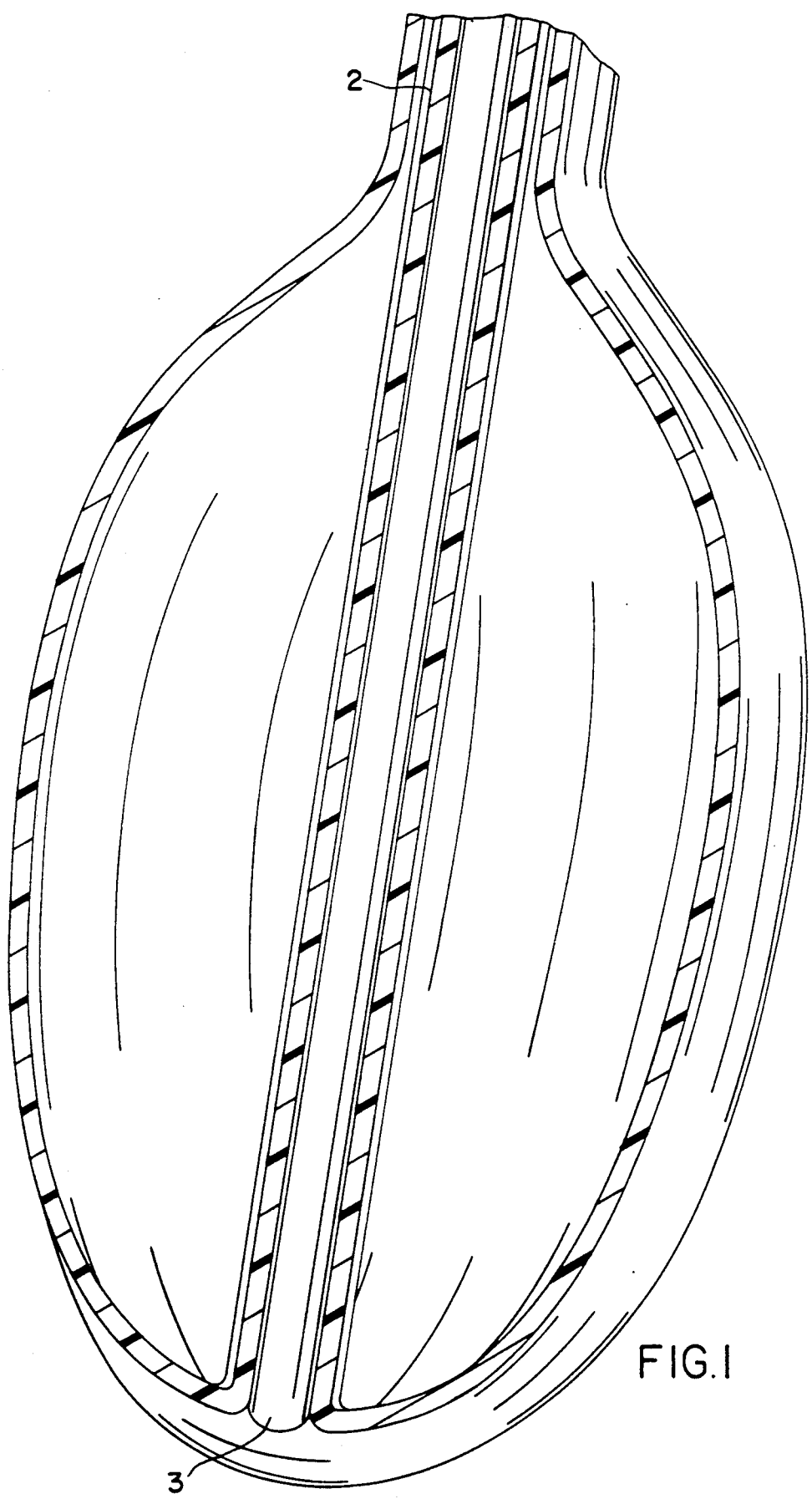
FIG. 1 shows the outer envelope of the bulb when it is inflated and depicts the device's open axial core.

Turning now to the drawings, the preferred embodiment is a device sized and formed for invasive intravenous medical treatment and constructed of plastic or other such flexible material whose distal end extremity has three separate, segment, segment-like chambers 1 which are oriented axially. There are ducts, or inflation lumens 2, leading from each such chambers that surround the open axial core 3 and run along the length of the catheter's tubing 4, to a set of pressure sources 5 that are attached to the other end of that tubing. Gas or liquid flows from these sources, through the respective lumens, to pressurize head-end chambers causing the extremity to distend. Since the physician must cause the catheter to be entered into a body cavity or must introduce (or "feed") it into a major vessel for traversal through the circulatory system, the catheter is constructed of material sufficiently stiff to cause such introduction yet is soft enough to allow the head to inflate.

Selective, variable pressurization causes the unequal expansion of the chambers 1 thereby causing the extremity to distend asymmetrically (about the device's axis). The angular position (about the catheter's axis) of the asymmetry is determined by which cell (or combination of cells) is selected to be inflated. The extent of that distension is determined by the amount of pressure in the cell. An embodiment of this invention with three head-end sector cells can produce asymmetric distension in any angular direction normal to the device's axis via the proper selection of cell for inflation.

The ability to effect such head-end asymmetry is important to this patent since it provides the facility to steer the catheter in the blood vessel by means of this asymmetry's creating a hydrofoil surface which produces a displacement force as it interacts hydrodynamically with the bloodstream flowing over it. The actual displacement force is a vector, essentially normal to the catheter's axis, whose magnitude and direction is a function of the amount and angular location of the catheter's asymmetric distension. It is this displacement force which causes the end of the catheter to be deflected within a patient's blood vessel to facilitate traversal over a tortuous path to the desired site of treatment or diagnosis. At that point such treatment or diagnosis is affected via any common invasive device that has been introduced by the user into the catheter's open core 3.

The catheter's open core 3 also can provide a source for externally monitoring blood pressure in the vessel at the distal end of the catheter as it is traversed through the circulatory system. This allows continual external monitoring of pressure at actual site of the distal-end extremity. Such monitoring can be important to the assessment of vessel constriction and its subsequent reduction through the invasive procedures herein described. Additionally, liquid or gas may be delivered from an external source to the internal site of the distal-end through such an open axial core.

Figure 2:
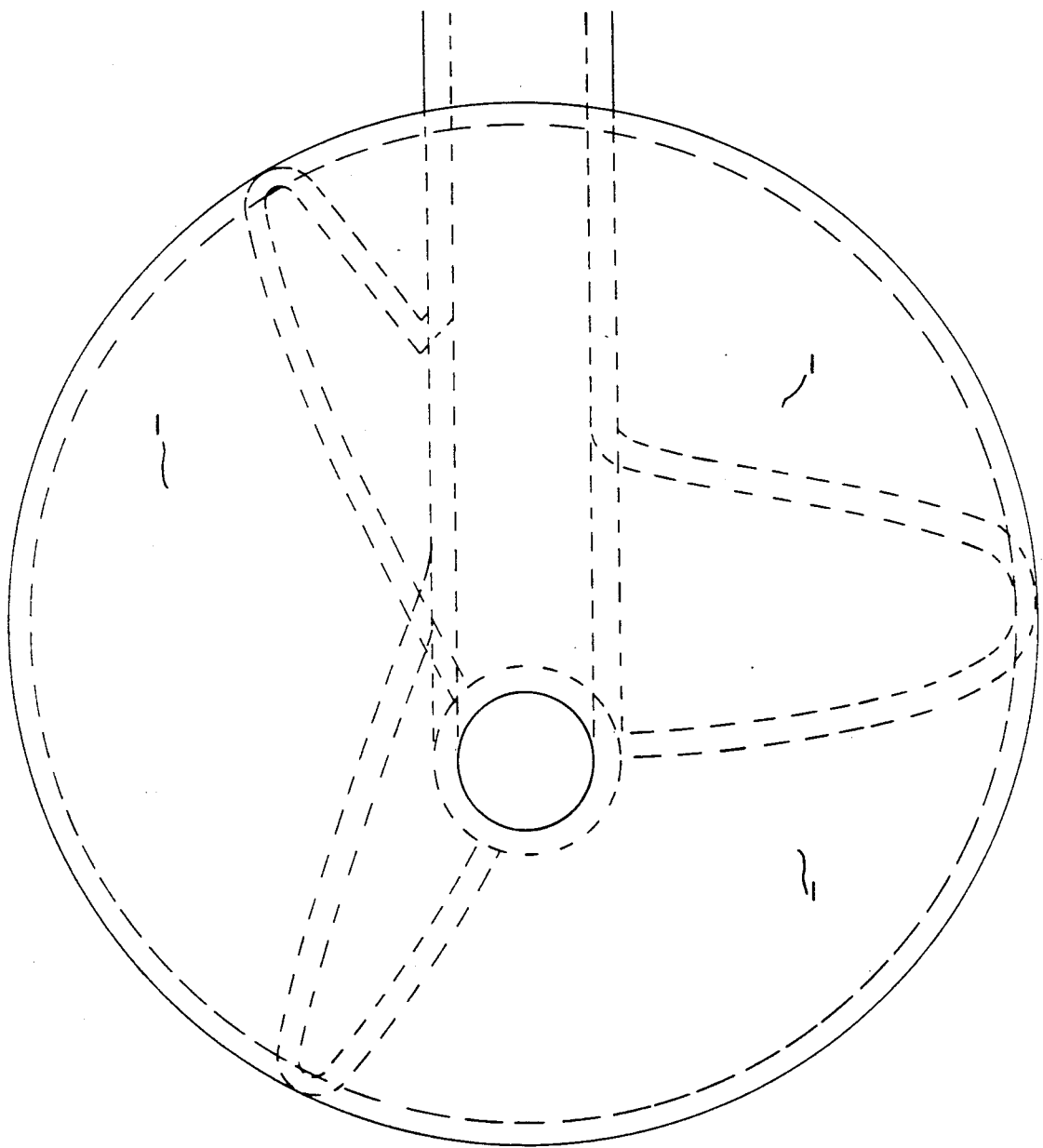
FIG. 2 shows a distal end view of the catheter depicting the three sector chambers.
Figure 3:
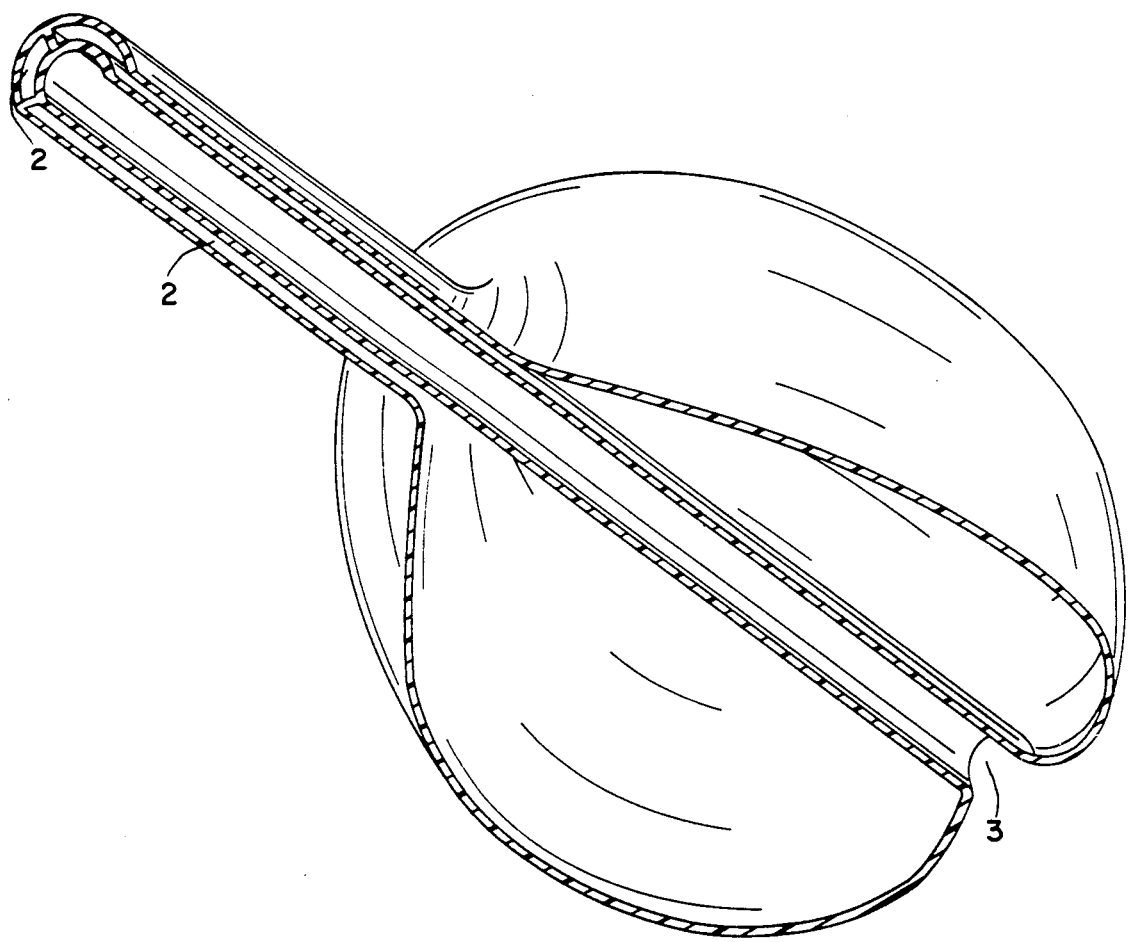
FIG. 3 shows a symmetrical distension from another viewing angle, and it also shows the deatils of the pressurization lumens and axial inner core.
Figure 4:
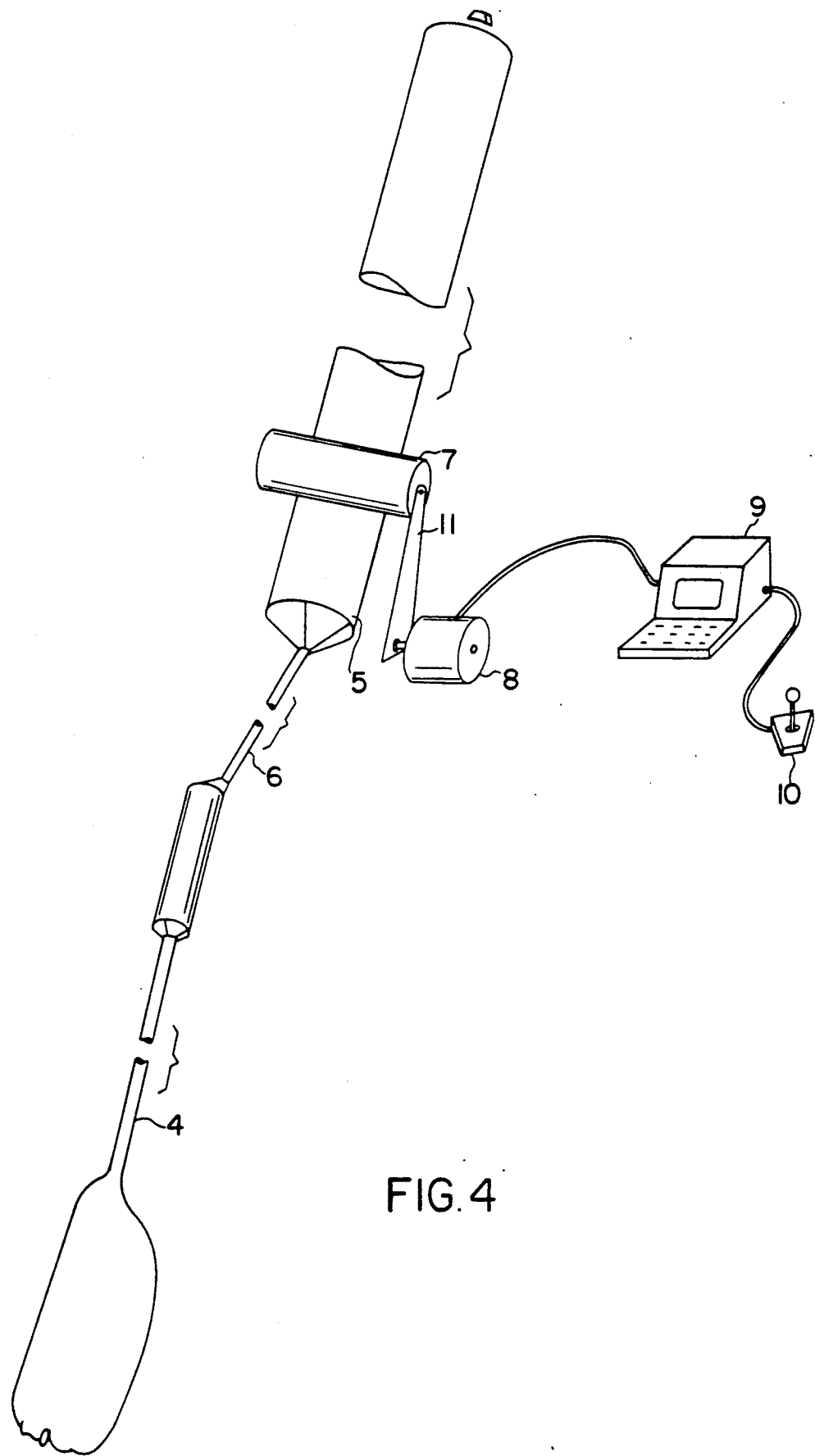
FIG. 4 shows one pressure source vessel cylinder, its connecting tubing, and the pressure effecting mechanism with its moveable pinch roller, servoactuator, microprocessor and joystick.

The device assembly consists of the multi-chambered distal end, FIG. 2, the elongated tube 4 (composed of the pressure lumens 2 surrounding the axial core 3), and the connecting feed tubes 6 that link the pressure lumens to the separately controlled pressure sources. One apparoach to such distal-end cell pressurization employs controlled gas sources to which the feed tubes are connected at time of catheter use.

An optional embodiment employs liquid vessels in the form of cylinders 5 (attached to the connecting tubes 6) that are compressed to pressurize the ducts. As such the entire device is formed, air is evacuated from it, each set of cylinders, feed tubes, ducts and head-end chambers is filled with liquid (e.g. sterile saline), then each cylinder is sealed and the complete unit is packaged. This more complex design, manufacturing and packaging approach enhances patient safety somewhat since its pressurization medium is in a completely closed system, filled at time of manufacture with a sterile fluid that the body can accept without harm in the highly remote event a catheter rupture might take place. In this embodiment, the actual controlled pressurization is effected through the movement of rollers 7 pressed down (pinched) onto the pressure cylinders 5. The rollers are moved via links 11 to servoactuators 8 which are connected to a microprocessor 9 which translates joystick 10 (or other input device) steering commands into appropriate movement of proper servoactuators.

In a representative application an incision is made, the catheter is introduced into the selected blood vessel and traversal through the vessel is begun. Fluoroscopic images are made at key points to follow traversal. Upon observing that a vessel bifurcation is encountered, the proper pressure source(s) is activated to distend the appropriate catheter head-end chamber(s) to produce (from the blood flowing over the asymmetrical hydrofoil shape) the desired displacement force. This displacement force causes the catheter to deflect into the desired blood vessel at the bifurcation. Entry into the proper vessel is verified by fluoroscopic image. The catheter is then guided, in like manner, further into the patient's circulatory system until it is positioned at the site of the target arterial restriction.

There, the restriction is reduced by curettage affected by the mechanisms contained optionally at its axial core and/or through ballon angioplasty procedure through symmetrical inflation of the catheter head-end. Where curettage is employed, the head-end cells are sequentially pressurized to cause an off-axis sweep of the curettage mechanism. Should balloon angioplasty be desired, the catheter is inflated into a balloon configuration by equally pressurizing all catheter chambers.

What is claimed is:

1. An invasive medical catheter comprising:
   a flexible elongated tubular member having proximal and distal ends;
   a balloon means attached to and encircling a portion of said elongated tubular member proximate said elongated member's distal end; said balloon means comprising an outer elastic member and having a plurality of inner independent cells each of which is connected to a corresponding inflation lumen such that each cell may be inflated independently to create an asymmetrical distension of the outer elastic member; each cell being defined by the encircled portion of said elongated tubular member, a portion of said outer elastic member, and two longitudinal wall members angularly spaced from one another and extending radially from said elongated tubular member to said outer elastic member;
   wherein said asymmetrical distension of the outer elastic member forms a hydrofoil outer surface whereby blood flowing over said hydrofoil surface imparts a deflection force on the catheter distal end.

2. The catheter of claim 1 wherein the tubular member includes an open core with openings at both the proximal and distal ends.

3. The catheter of claim 2 wherein the open core is sized to accommodate the insertion of various flexible axially-oriented medical devices.

4. The catheter of claim 3 wherein controlled off-axis deflection of the open core is accomplished as a derivative effect of the controlled asymmetrical distension of the catheter's distal-end structure.

5. The catheter according to claim 1 further including a plurality of connecting tubes connected to said inflation lumens at one end and to sources of independently controlled, pressurized medium at the other end to conduct said pressurizing medium to respective inflation lumens and in turn to the respective inner cells.

6. The catheter of claim 1 wherein pressure vessels in the form of cylinders are connected to the inflation lumens through a plurality of connecting tubes.

7. The catheter of claim 6 wherein air is evacuated at the time of manufacture from the pressure vessels, connecting tubes, inflation lumens, and inner cells, each of which is then filled with a sterile liquid and sealed.

8. The catheter of claim 6 wherein inflation of an individual inner cell is achieved by forcing fluid from its respective pressure vessel through its connecting tube, through its inflation lumen, and into the inner cell.

9. The catheter of claim 8 wherein fluid is forced from a pressure vessel by moving a roller which is squeezed upon the vessel; said roller being arranged such that its axis is normal to the axis of the vessel and its movement is along the axis of the vessel.

10. The catheter of claim 9, wherein said movement is affected by a servoactuator attached to said roller, wherein said servoactuator is controlled by a microprocessor containing coded instructions which translate steering commands from a catheter maneuvering operator into appropriate servoactuator directives which consequently impart the desired steerings.

11. The catheter of claim 1 wherein the balloon means outer elastic member has a circular cross-section when each inner cell is equally pressurized for performing angioplasty.

* * * * *